(12) United States Patent
Davey et al.

(10) Patent No.: US 6,527,695 B1
(45) Date of Patent: Mar. 4, 2003

(54) MAGNETIC STIMULATION COIL AND CIRCUIT DESIGN

(75) Inventors: Kent R. Davey, New Smyrna Beach, FL (US); Charles Epstein, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/676,119

(22) Filed: Sep. 29, 2000

Related U.S. Application Data
(60) Provisional application No. 60/175,504, filed on Jan. 11, 2000.

(51) Int. Cl.[7] .................................................. A61N 1/00
(52) U.S. Cl. ........................................................ 600/13
(58) Field of Search .............................. 600/13, 9, 10, 600/11, 12, 14, 15, 407, 410

(56) References Cited

U.S. PATENT DOCUMENTS

| | | | | |
|---|---|---|---|---|
| 4,940,453 A | * | 7/1990 | Cadwell | ........................ 600/13 |
| 5,350,414 A | * | 9/1994 | Kolen | ........................ 607/62 |
| 5,984,854 A | * | 11/1999 | Ishikawa et al. | ............... 600/9 |

* cited by examiner

Primary Examiner—Kevin Shaver
Assistant Examiner—Brian Szmal
(74) Attorney, Agent, or Firm—Levisohn, Lerner, Berger & Langsam (57) ABSTRACT

The invention is a method for nerve cell stimulation wherein optimal frequency of a coupled magnetic circuit, optimal reluctance of a coupled magnetic circuit, optimal capacitance of a coupled magnetic circuit, and optimal winding resistance of a coupled magnetic circuit for construction of a magnetic nerve stimulator are selected to maximize stimulation of a nerve cell. The maximization of the nerve stimulation is achieved by maximizing the membrane voltage.

10 Claims, 12 Drawing Sheets

MAGNETIC STIMULATION COIL AND CIRCUIT DESIGN

RELATED APPLICATIONS

This application claims the priority of U.S. Provisional Application Ser. No. 60/175,504, filed Jan. 11, 2000, the disclosure of which is incorporated herein by reference.

FIELD OF THE INVENTION

The present invention relates generally to the field of electromagnetic nerve stimulation. More specifically the present invention relates to a method and apparatus for nerve stimulation using optimal efficient parameters for the electrical charging circuit.

BACKGROUND OF THE INVENTION

Electrical stimulation has been successfully tested clinically for multiple applications tracing its roots back to the late 1800's where it was applied in the stimulation of the peripheral facial muscles by George Duchenne de Boulogne, see M. S. George, "Re-animating the face: early writings by Duchenne and Darwin on the neurology of facial emotion expression", *J. Hist. Neurology*, vol.2, 1994, pp. 1–13. Since then it has been used for muscle rehabilitation (see e.g., G. A. Dudley, "Is electrical stimulation applicable to increase strength and power in normal humans?", in *Human Muscular Function During Dynamic Exercise*, ed. by P. Marconnet, B. Saltin, P. Komi, and J. Pootmans, Karger Book Series: Medicine and Sport Science, Karger Publications, Basel, 1996, pp. 71–81), bed sore treatment, incontinence, and general diagnostics to mention only a few of its applications. Excitations that are repeated demand higher efficiency. Greater efficiency translates into lighter and smaller power supplies, and longer life for implantable devices.

Magnetic stimulation is only now catching up to electrical stimulation in terms of clinical uses. Early uses of MS were principally devoted to diagnostics, a good review of which is found in E. M. Wasserman, L. M. McShane, M. Hallett, and L. G. Cohen, "Noninvasive mapping of muscle representations in human cortex", *Electroencephalography and Clinical Neurophysiology*, vol. 85, 1992, pp. 1–8. More recently rapid transcranial magnetic stimulation (rTMS) is being used in speech diagnosis, see e.g., C. M. Epstein, J. K. Lah, K. Meador, J. D. Weissman, L. E. Gaitan, B. Dihenia, "Optimum stimulus parameters for lateralized suppression of speech with magnetic brain stimulation", *Neurology*, vol. 44, 1994, pp. 269–273. It is also being successful employed in the treatment of severe clinical depression, see e.g., A. Fleischman, K. Prolov, J. Abarbanel, R. H. Belmaker, "Effect of Transcranial magnetic stimulation on behavioral models of depression", *Brain Research*, vol. 699, 1995, pp. 130–132 and B. Greenberg, U. McCann, J. Benjamin, D. Murphy, "Repetitive TMS as a probe in Anxiety Disorders: Theoretical Considerations and Case Reports", *CNS Spectrums*, vol.2, no. 1, 1997, pp. 47–52. As more applications of the rapid magnetic stimulation surface, the issues of efficiency both within the body and the stimulation circuit arise.

In 1991 Barker, et. al., wrote a study on the effect of waveform efficiency in determining neural membrane efficiency. See A. Barker, C. Graham, and I. Freeston, "Magnetic nerve stimulation: the effect of waveform on efficiency, determination of neural time constants, and the measurement of stimulator output", *Magnetic Motor Stimulation: Basic Principles and Clinical Experience*, EEG Supplemental 43, 1991, pp. 221–237. Following the suggestion of Plonsey, R. Plonsey, *Bioelectrical Phenomena*, McGraw Hill, New. York, 1969, Barker et. al. modeled the nerve membrane as a parallel capacitance and resistance, with an intracellular and extracellular resistance providing the closure path for any induced or injected currents. The energy necessary to achieve threshold stimulation was measured as a function of B field rise time. Threshold stimulation energy continued to drop with reduced rise time of the resonance frequency of the magnetic stimulator. Their methods were useful in predicting nerve membrane time constants.

Magnetic stimulation requires moving enough charge through an electrically sensitive nerve membrane to depolarize it, see, e.g. John Cadwell, "Optimizing Magnetic Stimulator Design", *Magnetic Motor Stimulation: Basic Principles and Clinical Experience*, EEG Supplement 43, 1991, pp. 238–248; this means that the membrane voltage must be increased from its normal resting negative potential. Many authors have attempted to offer guidelines for producing energy efficient stimulation coils, as well in the modeling of these coils. See e.g., G. A. Mouchawar, J. A. Nyenhuis, J. D. Bourland, and L. A. Geddes, "Guidelines for energy efficient coils: coils designed for magnetic stimulation of the heart", *Magnetic Motor Stimulation: Basic Principles and Clinical Experience*, EEG Supplement 43, 1991, pp. 255–267; C. W. Hess, K. M. Rosler, R. O. Heckmann, H. P. Ludin, "Magnetic Stimulation of the Human Brain: Influence of size and shape of the stimulating coil", *Motor Disturbances II*, Academic Press Limited, London, U.K. 1990, pp. 31–42; A. Cantano, P. Noel, "Transcranial Magnetic Stimulation: Interest in the excitation threshold", Acta Neurologica Belgica, vol. 97, 1997, p. 61; G. Cerri, R. Deleo, F. Moglie, A. Schiavoni, "An accurate 3-D model for magnetic stimulation of the brain cortex", *Journal of Medical Engineering and Technology*, Vol. 1, 1995, pp. 7–16. Roth and Basser, B. J. Roth and P. J. Basser, "A model of the stimulation of a nerve fiber by electromagnetic induction", *IEEE Transactions on Biomedical Engineering*, vol. 37, 1990, pp. 588–596, were among the first to actually model the stimulation of a single fiber by electromagnetic induction. However, there is still a substantial interest in the art for a method of nerve stimulation using optimal efficient parameters of the electrical charging circuit.

SUMMARY OF THE INVENTION

It is an object of the present invention to provide a method for nerve stimulation wherein a coil design and its parameters are chosen from coupling analytically the electromagnetic circuit to that within the nerve.

Other objects, advantages and features of this invention will be more apparent hereinafter.

The present invention provides a method for nerve cell stimulation, comprising selecting an optimal frequency of a coupled magnetic circuit for construction of a magnetic nerve stimulator, selecting an optimal reluctance of a coupled magnetic circuit for construction of a magnetic nerve stimulator, selecting an optimal capacitance of a coupled magnetic circuit for construction of a magnetic nerve stimulator, and selecting an optimal winding resistance of a coupled magnetic circuit for construction of a magnetic nerve stimulator. In the preferred embodiment, the optimal frequency, optimal reluctance, optimal capacitance and/or the optimal winding resistance are selected to maximize stimulation of a peripheral nerve cell, or any other type of nerve cell, using the methods provided herein.

BRIEF DESCRIPTION OF THE DRAWINGS

A full understanding of the invention can be gained from the following description of the preferred embodiment when read in conjunction with the accompanying drawing in which.

DETAILED DESCRIPTION OF THE PREFERRED EMBODIMENT AND THE DRAWINGS

Figure 1:
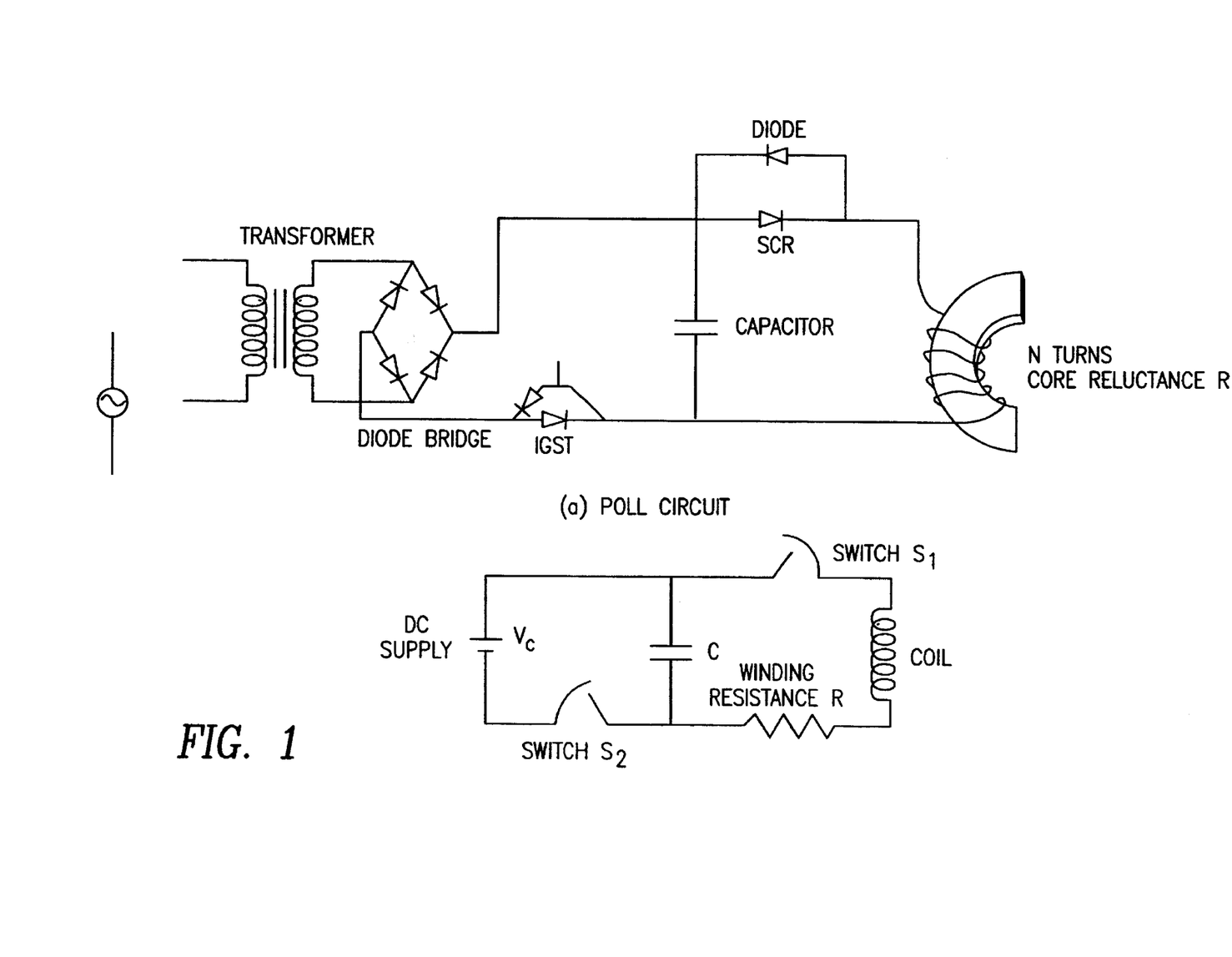
FIG. 1 is a schematic diagram for an electrical circuit for an iron core magnetic stimulator.

The power electronics of electromagnetic stimulator devices revolves around a capacitor driving current into the inductance of the stimulator core. The stimulator circuit is depicted in FIG. 1 with inset (a) being the full circuit, and inset (b) being a simplified equivalent. A dc charged capacitor C is allowed to resonate a complete cycle with the inductance comprising the core head. Were there no winding resistance, this would mean that the capacitive energy ½ $CV^2$ would shift to inductive energy ½ $LI^2$, and then reverse back into the capacitor; the full wavelength would require a time $$\tau = 2\pi\sqrt{LC}. \tag{1}$$

Figure 2:
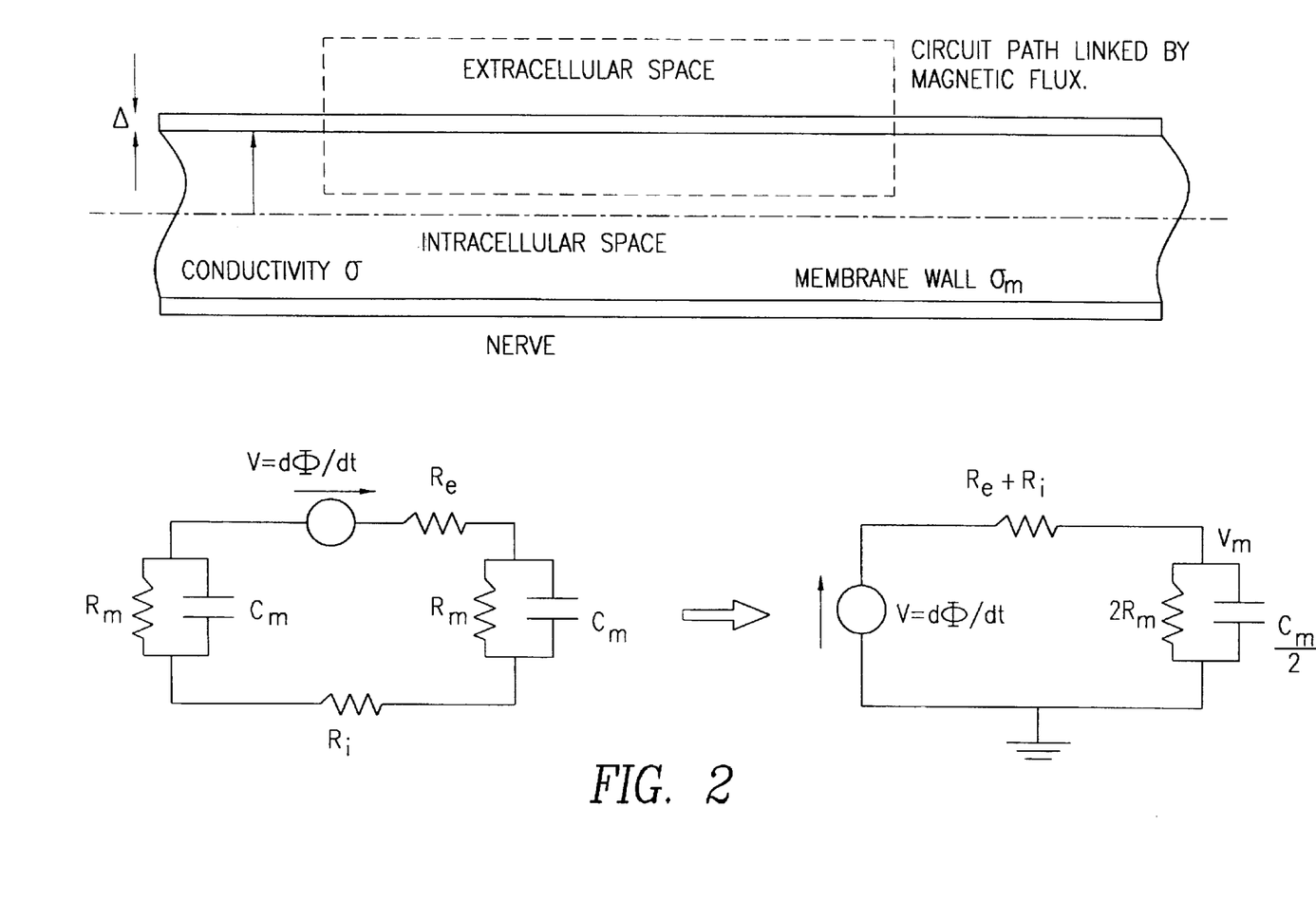
FIG. 2 is a schematic diagram of biological tissue demonstrating how a changing magnetic flux induces a voltage within a nerve fiber.

The magnetic flux from the inductor core is driven into biological tissue; the time changing flux will induce a voltage through the tissue linked by the flux. Of course only a fraction of that flux will link a circuit comprised of the intracellular and extracellular space around a nerve through the membrane wall. This biological circuit is depicted in FIG. 2. The induced voltage is only a fraction of the flux linking the iron core winding. The membrane is characterized by a low permeability/mobility to ion flow in its resting state. Note that the model focuses on a sub-threshold state over a long nerve length. The capacitance of the membrane wall can be expressed in terms of its permittivity $\epsilon$ for a per unit axial length l as $$C_m = \frac{\varepsilon 2\pi r l}{\Delta}. \tag{2}$$

The membrane resistance $R_m$ can be expressed in terms of the membrane wall thickness $\Delta$ as $$R_m = \frac{\Delta}{\sigma_m 2\pi r l}. \tag{3}$$

The intracellular resistance per unit length l is $$R_i = \frac{l}{\sigma_i \pi r^2}. \tag{4}$$

The extracellular resistance $R_e$ is very small since the volume of the extracellular space is large.

By solving both a magnetic circuit and a coupled biological circuit the optimal parameters of the circuit design will be found. Because the current in the biological tissue is very small, the problem is not truly a coupled circuit problem since the biological circuit current does not affect the magnetic circuit. The current i in the magnetic circuit satisfies the differential equation $$L\frac{di^2}{dt^2} + R\frac{di}{dt} + \frac{i}{C} = 0, \tag{5}$$

$$\frac{di}{dt}(t=0) = \frac{V_C}{L}, \, i(t=0) = 0.$$

Taking the Laplace transform and using I(s) for the transformed current yields the following $$I(s) = \frac{V_C}{Ls^2 + Rs + \frac{1}{C}} \tag{6}$$

The flux linking the magnetic core winding is a function of the reluctance $\mathfrak{R}$ of the magnetic circuit and the turns N as $$\Phi = \frac{NI}{\mathfrak{R}} \tag{7}$$

The induced voltage in the biological circuit will be related to a small fraction f of the total flux through its time rate of change; in Laplace domain space, this becomes $$V_{ind} = \frac{d}{dt}\left(\frac{fNI}{\mathfrak{R}}\right) = \frac{sfNI(s)}{\mathfrak{R}}. \tag{8}$$

Thus the induced voltage becomes $$V_{ind}(s) = \frac{sfNV_C/\mathfrak{R}}{Ls^2 + Rs + \frac{1}{C}}. \tag{9}$$

Of particular interest is the nerve membrane voltage $V_m$. Kirchoff's voltage law written for the biological circuit is $$\frac{V_m - V_{ind}}{R_i + R_e} + \frac{V_m C_m s}{2} + \frac{V_m}{2R_m} = 0. \tag{10}$$

Rearranging terms yields the result $$V_m = \frac{fsNV_C \big/ \Re\left(\frac{2R_m}{2R_m + R_i + R_e}\right)}{\left(Ls^2 + Rs + \frac{1}{C}\right)(1 + s\tau_m)}, \tag{11}$$

where $\tau_m = \frac{C_m R_m (R_i + R_e)}{2R_m + R_i + R_e} \approx C_m R_m = \frac{\varepsilon}{\sigma_m}$.

Here the limit has been taken for large l, where $\tau_m$ is dependent only on the constitutive properties of the membrane. The energy W delivered to the magnetic circuit is $$W = \tfrac{1}{2}CV_C^2, \tag{12}$$

and the resonant resistance free frequency is $$\omega = \frac{1}{\sqrt{LC}}. \tag{13}$$

In terms of these variables the numerator multiplier of (11) can be rewritten in terms of energy as $$sfNV_C / \Re = sf\sqrt{\frac{L}{R}}\, V_C = sf\frac{\sqrt{LC}\sqrt{C}\, V_C}{C\sqrt{R}} = sf\frac{\sqrt{2W}\,\omega L}{\sqrt{R}}. \tag{14}$$

Here use has been made of the fact that $L = N^2 \Re$. For very short nerve fibers, $R_m$ is a dominant resistance, but for very long fibers with large l, the limit examined in (11), $$\frac{2R_m}{2R_m + R_i + R_e} \approx \frac{2R_m}{R_i}. \tag{15}$$

Figure 3:
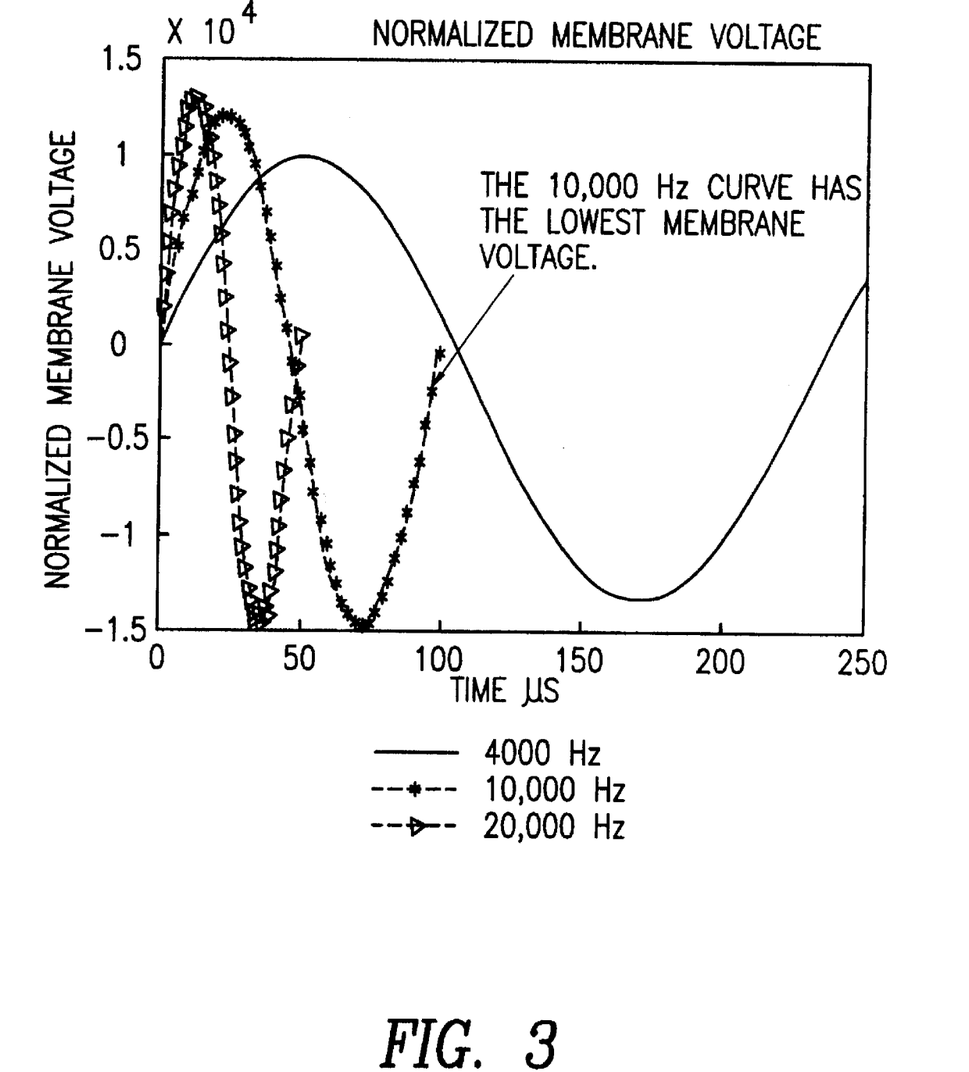
FIG. 3 is a graph showing normalized membrane voltage for three resonant frequencies.

For what follows, the resistance ratio $(2\,R_m)/R_i$ will be absorbed into the factor f. Finally, the membrane voltage can be written in terms of the circuit energy W and the resonant frequency $\omega$ as $$V_m(s) = \frac{sf\sqrt{2W}\,\omega / \sqrt{R}}{\left(s^2 + \frac{s}{\tau_L} + \omega^2\right)(1 + s\tau_m)}, \tag{16}$$

where the term $\tau_L$ has been introduced to represent the L/R time constant. The inverse Laplace transform delivers the membrane voltage as a function of time, Since (17) is quite detailed, it is best to examine $V_m$ for a fixed energy W and magnetic reluctance $\Re$. The normalized membrane voltage Vm/f versus time for three resonant frequencies is quite instructive. Typical circuit values are R=12.6 mΩ, L=20 μH, and $\tau_m$=100 μs. The membrane voltage for these parameters is shown in FIG. 3. Note that the absolute value of the second negative peak is greater than the first positive peak. Also note that the middle resonant frequency has the lowest negative peak. This is a direct result of the membrane capacitance.

The problem can be simplified considerably by ignoring resistive loss which hastens the waveform decay. In this limit, the membrane voltage becomes $$V_m = f\omega\sqrt{\frac{2W}{R}}\,\frac{\left(\cos(\omega t) + \omega\tau_m \sin(\omega t) - e^{-\frac{t}{\tau_m}}\right)}{1 + \omega^2 \tau_m^2}. \tag{18}$$

Care should be exercised in the use of (18). It is only valid when the resistance is small. All forthcoming plots except FIG. 4 and FIG. 7 of this paper are computed using (17).

Figure 4:
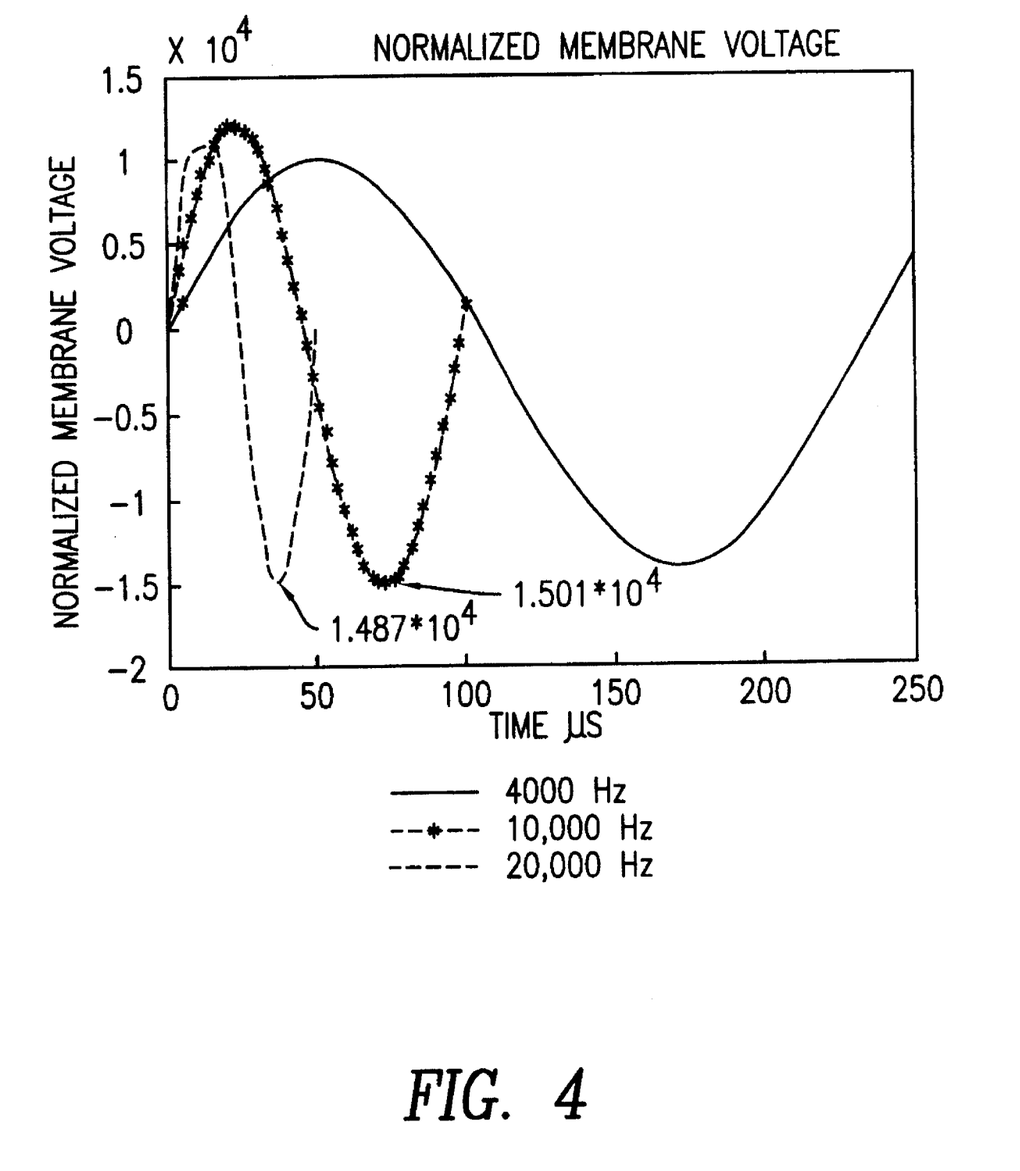
FIG. 4 is a graph showing normalized membrane voltage with no magnetic circuit winding resistance for three resonant frequencies.

The equivalent plot to that of FIG. 3 without loss is shown in FIG. 4. Because the resistance is small, little is changed. It is clear that the membrane capacitance contributes to the exponential decay term in (18). This is the reason that the second negative phased pulse is deeper than the positive going wave. As with FIG. 3, an optimal resonant frequency occurs between the extremes of 4 kHz and 20 kHz, with a small monotonic decrease witnessed after 10 kHz. Note that this analysis ignores sodium and potassium gate phenomena which will add additional uncertain time dependent processes.

The numerator is a transcendental equation with no analytical solution for a minimum. The terms $\cos(\omega t) + \omega\tau_m \sin(\omega t)$ have a minimum when $$\min\{\cos(\omega t) + \omega\tau_m \sin(\omega t)\} \text{ occurs when} \tag{19}$$

$$t = \frac{\pi + \tan^{-1}(\omega\tau_m)}{\omega}.$$

Figure 5:
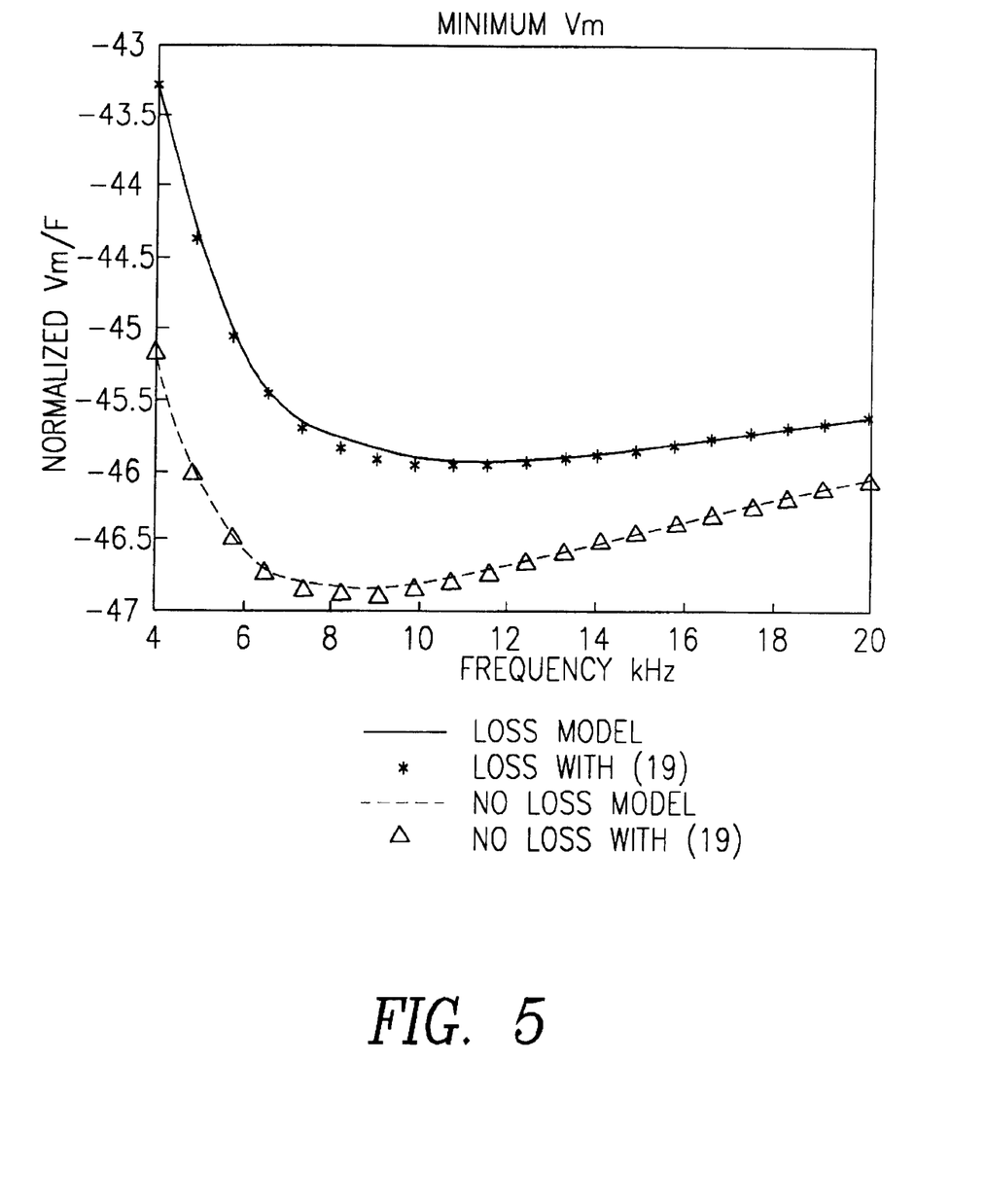
FIG. 5 is a graph showing minimum membrane voltage as a function of resonant frequency.

Equation (17) or (18) can be plotted for a band of resonant frequencies, seeking normalized Vm/f at the time consistent with (19). As an example, fix the inductance, reluctance, and resistance to 21.8 μH, 5.55 $10^6$H$^{-1}$, and 12.6 mΩ (6.1 m of #8 copper wire), respectively. Even with this resistance the absolute value of the second negative, $3^{rd}$ quarter minimum is 23% larger than the maximum of the first quarter wave peak. A graph is obtained by allowing the capacitance to span a range of values, but scaling the voltage as the inverse square root of capacitance so the energy remains fixed at 84.4 J. The result for $\tau_m$=125 μs is a plot closely delivering the optimal circuit resonance frequency, as shown in FIG. 5. The results are computed with and without losses, and clearly indicate that a lossy system has a higher optimal $$V_m(t) = f\sqrt{\frac{2W}{R}}\,\omega\tau_L \frac{(4\omega^2\tau_L^2 - 1)\left(e^{-\frac{t}{2\tau_L}}\cos(\beta) + \frac{e^{-\frac{t}{2\tau_L}}(2\tau_L\tau_m\omega^2 - 1)\sin(\beta)}{\sqrt{4\omega^2\tau_L^2 - 1}} - e^{-\frac{t}{\tau_m}}\right)}{4\omega^4\tau_m^2\tau_L^3 + \omega^2(4\tau_L^2 - \tau_m^2\tau_L) + (\tau_m - \tau_L)}, \tag{17}$$

where $\beta \equiv \frac{1}{2}\sqrt{\frac{4\omega^2\tau_L^2 - 1}{\tau_L^2}}\,t$.

frequency; the higher frequency allows less time for the exponential L/R decay to dampen the induced membrane voltage. The plots were computed directly over a range of frequencies, with the minimum voltage computed using (19). The close agreement demonstrates the accuracy of (19) in predicting the peak even in a lossy context. Remember that the negative peaks are being plotted. The plot would suggest that a resonant frequency closer to 10 kHz would be ideal for realizing excitation with the smallest energy for this nerve fiber with $\tau_m=125\,\mu s$. However component restrictions frequently begin to cause problems before that limit is reached.

Figure 6:
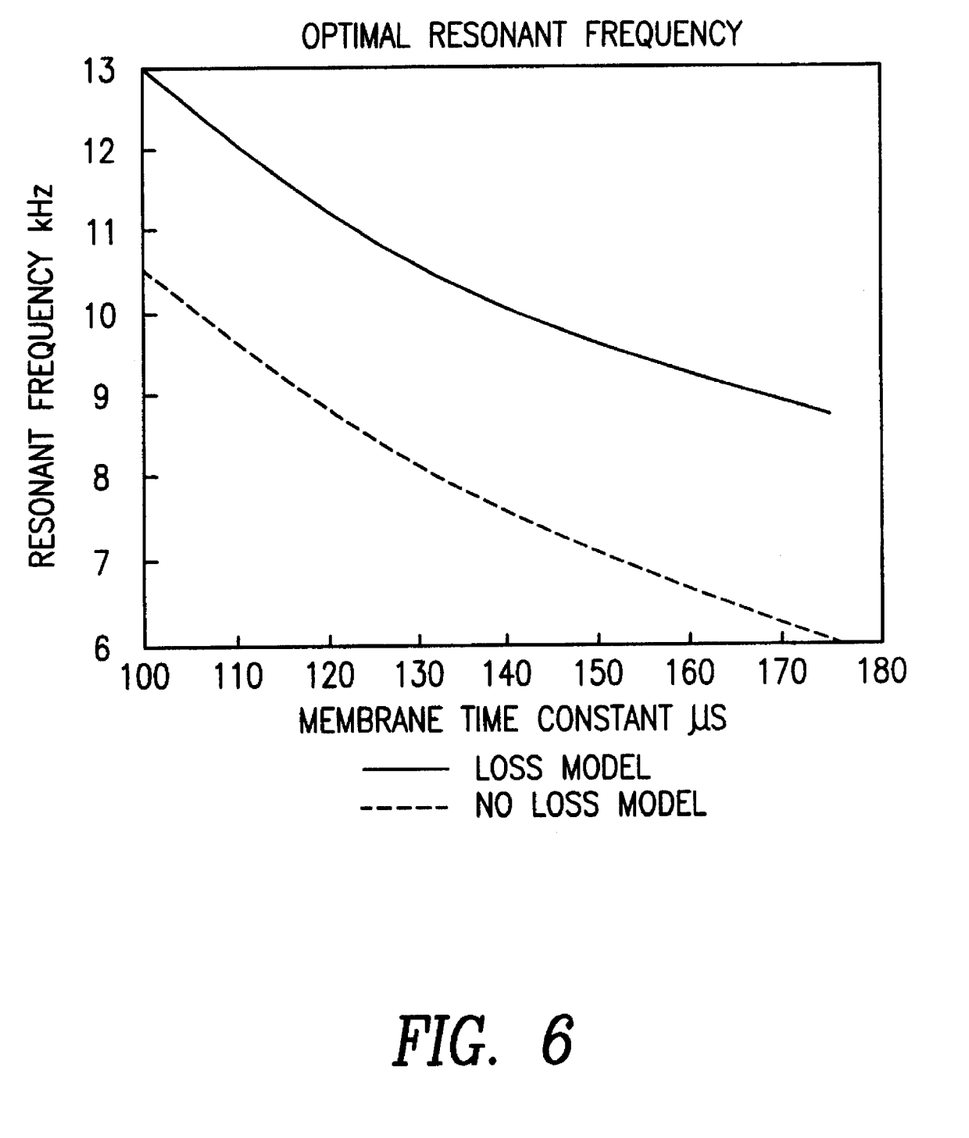
FIG. 6 is a graph showing optimal resonant frequency as a function of membrane time constant $\tau_m$.

Barker's results (See, Magnetic Nerve Stimulation: the Effect of Waveform on Efficiency, Determination of Neural Time Constants, and the Measurement of Stimulator Output, Table III) indicated that the time constants $\tau_m$, obtained through threshold stimulation on a number of patients, ranged from $\tau_m=121\pm23\,\mu s$ for peripheral nerve stimulation to $\tau_m=152\pm26\,\mu s$ for cortical nerve stimulation. These ranges considered different degrees of stimulation as well. Shown in FIG. 6 is the optimum circuit resonant frequency as a function of membrane time constant $\tau_m$, plotted with and without losses, with the lossy circuit delivering the higher optimal resonant frequency. The resistance, inductance, and energy parameters are identical to FIG. 5. It is clear from (11) that small nerve fibers have large values of $\tau_m$. Note that these results are obtained for normalized membrane voltage, Vm/f.

Figure 7:
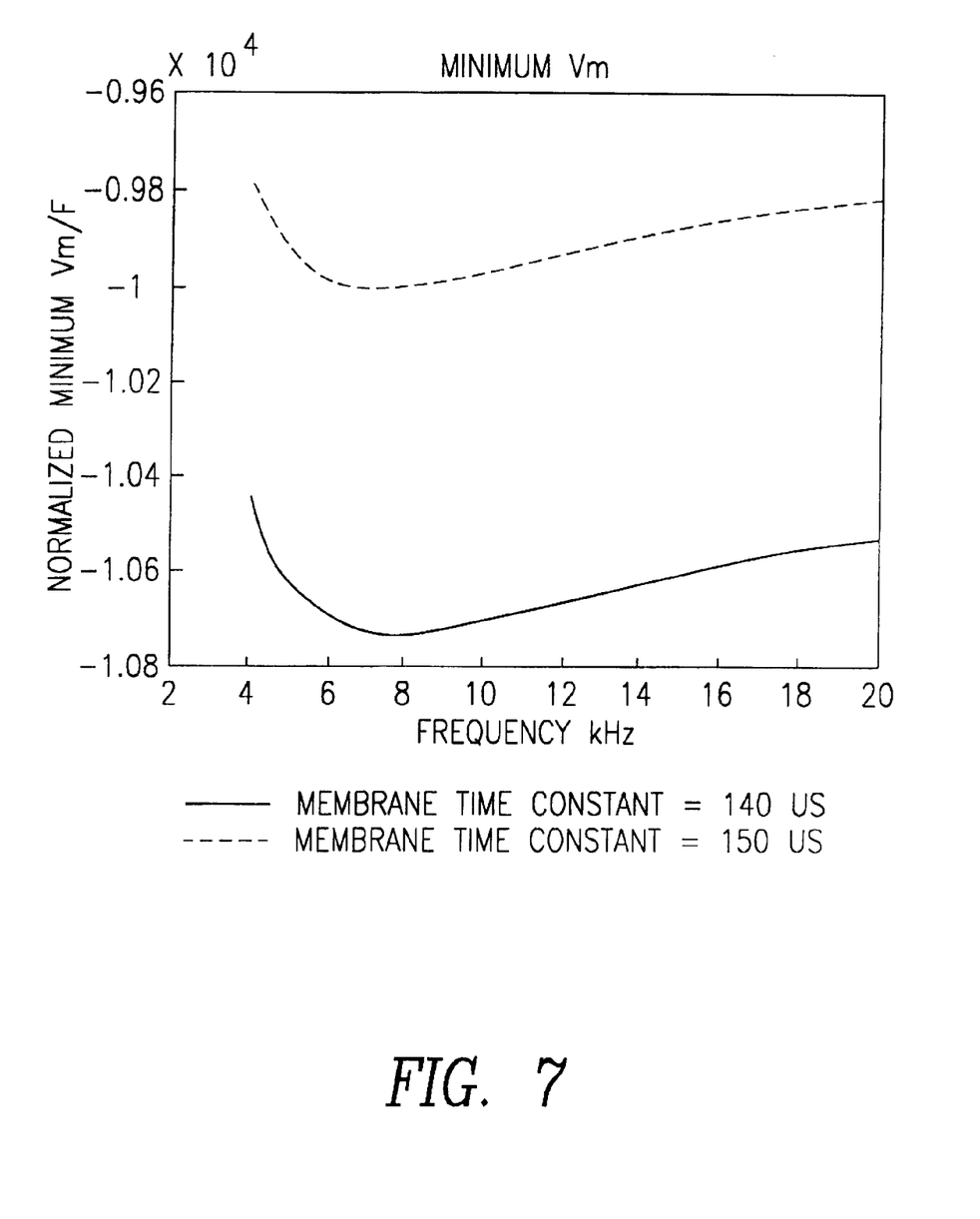
FIG. 7 is a graph showing membrane voltage $V_m$ as a function of resonant frequency.

Shown in FIG. 7 is the minimum negative peak for $V_m$ as a function of resonant frequency, assuming the resistance of the winding is minimal. The larger time constant, 150 $\mu s$, corresponds to a smaller fiber. The first important observation is that the negative peak of the larger nerve fiber is greater than that of the smaller fiber with the higher time constant $\tau_m$ as expected, since smaller fibers are known to be more difficult to stimulate. The second observation is that the smaller nerve fiber has a smaller optimal resonance frequency.

The results summarized in (17) and (18) lead to several important conclusions. To maximize nerve cell stimulation the following should be observed:
1. Maximize the energy.
2. Minimize the reluctance consistent with the target depth. The outer radius of the core should be no smaller than the desired depth. The choice of the inner radius depends on a optimized balance between decreasing the reluctance and decreasing the resistance.
3. Aspire towards a high resonant frequency taking into account the size of the nerve fiber, and target region; in a typical lossy circuit this optimal resonant frequency is likely to be between 9 and 11 kHz.
4. Use a biphasic excitation circuit, since the membrane capacitance will always ensure a deeper membrane dip using representative resistances during the second portion of the wave. This result is supported by the recent empirical data of Maccabee. (See, P. J. Maccabee, S. S. Nagarajan, V. E. Amassian, D. M. Durand, R. Q. Cracco, A. Z. Szabo, A. Ahad, K. S. Lai, and L. P Eberle; "Optimal Polarity Sequence for Exciting Human and Porcine Peripheral Nerve with Neuromagnetic Stimuli: with Computer Simulation", *Journal of Physiology* (London), Vol. 513, No. 2, 1998, pp. 571–585).

Recommendations 1 and 3 are prone at the present time to be limited by hardware. The switching apparatus and insulation requirement considerations limit:
a. the maximum operating voltage, $V_C$,
b. the maximum operating current, I, and
c. the maximum resonance frequency, $\omega$, that can safely be used to shut off the thyristor before a double firing of that component is witnessed. This number is close to 5 kHz for present state of the art stud mounted SCR devices per manufacturer's recommendations (e.g., Power x). Their turn off time for a half cycle is about 90 $\mu s$.

When the voltage $V_C$, I, and $\omega$ are limited, the components for the stimulator are fixed. As will be shown shortly, the number of turns N does not affect the stimulation voltage, but lowering the exciting circuit resistance will help increase the membrane voltage. This supports the argument for lowering the number of turns, thus forcing the circuit designer to make the maximum current, I, as large as possible.

Suppose that the FDA (U.S. Food and Drug Administration) and component limitations suggest the three following limitations: V=2 kV, I=3 kA, and a complete cycle angular frequency $$\omega = \frac{2\pi}{200\,\mu s} = 31,416. \tag{20}$$

Thyristor shutoff times can be a limiting factor of how high the resonant frequency can be raised. If possible the designer should design for the frequency dictated by FIG. 6. (Power x is stating that new hockey puck SCR's are becoming available with a full cycle time constant of 80–90 $\mu s$, shut off time 40 $\mu s$). The reluctance of the core should be as small as possible. Some art is involved in the core design since this has to do with tissue depth and target span area. Analytically, the reluctance is the magnetic length divided by the product of the core area and circuit permeability, however it must be computed numerically using boundary or finite element software for any accuracy. A typical value for a transcranial brain stimulator half toroid spanning 220° and made of 3% grain oriented steel is 5.55 $10^6$ $H^{-1}$. The two constraints to be enforced are related to energy and resonant frequency, such that $$\tfrac{1}{2}CV^2=\tfrac{1}{2}LI^2, \tag{21}$$

$$\omega = \frac{1}{\sqrt{LC}}. \tag{22}$$

Combining these two constraints yields the capacitance C and inductance L as $$C = \frac{I}{V\omega} = 47.75\,\mu F, \tag{23}$$

$$L = \frac{V}{I\omega} = 21.22\,\mu H. \tag{24}$$

In terms of the above computed reluctance, the number of turns would be $$N=\sqrt{L\mathfrak{R}}=\sqrt{(21.22*10^{-6})(5.55*10^6)}=10.85\text{ turns.} \tag{25}$$

This would be the 'ideal' component selection for these conditions. The only way to further improve the nerve stimulation would be to ensure that the field from the laminated iron links the target region more effectively, thereby reducing the reluctance $\mathfrak{R}$. An adjustment of the turns would be necessary in that event.

The reluctance is obtained using a boundary element or finite element code to find the inductance of a 1-turn winding carrying the full set of amp-turns under saturation. The design of the core is determined by the width and depth of the target region and the weight constraint suggested by the physician. For TMS applications the core is positioned near a motor threshold point manually, and must be manageable by hand. Getting the reluctance in practice is an iterative process, beginning with a guess of the number of turns. The numerical code returns the reluctance and the turns then follow through (25). The amp-turns are updated and the process repeats to obtain the reluctance under saturation. These numerical procedures and the core shape are beyond the scope of this document.

A number of erroneous conclusions may result from focusing solely on the exciting circuit and ignoring the membrane capacitance. Suppose all membrane effects are ignored. The induced membrane voltage in the circuit of FIG. 2 will be proportional to the time rate of change of flux $$\frac{d\Phi}{dt}.$$

This quantity can be rearranged in terms of the capacitor voltage $V_C$ as $$\frac{d\Phi}{dt} = \omega \frac{NI}{\Re} = \frac{NI}{\Re} \frac{1}{\sqrt{LC}} = \frac{N}{\Re} V_C \sqrt{\frac{C}{L}} \frac{1}{\sqrt{LC}} = \frac{N}{\Re} \frac{V_C}{L}. \quad (26)$$

Since inductance can be represented by N and $\Re$ as $$L = \frac{N^2}{\Re}, \quad (27)$$

the final conclusion would result as $$\frac{d\Phi}{dt} = \frac{V_C}{N}. \quad (28)$$

Among the erroneous conclusions drawn from (28) would be that:
1. Changing the charging circuit capacitance would have no effect on nerve stimulation.
2. Changing the magnetic reluctance $\Re$ would have no effect on nerve stimulation. Increasing the capacitance has no effect at all on the membrane voltage. Increasing the capacitance will increase the energy, but decrease the frequency proportionately.
3. Decreasing the number of turns should help stimulate more nerve fibers.

Figure 8:
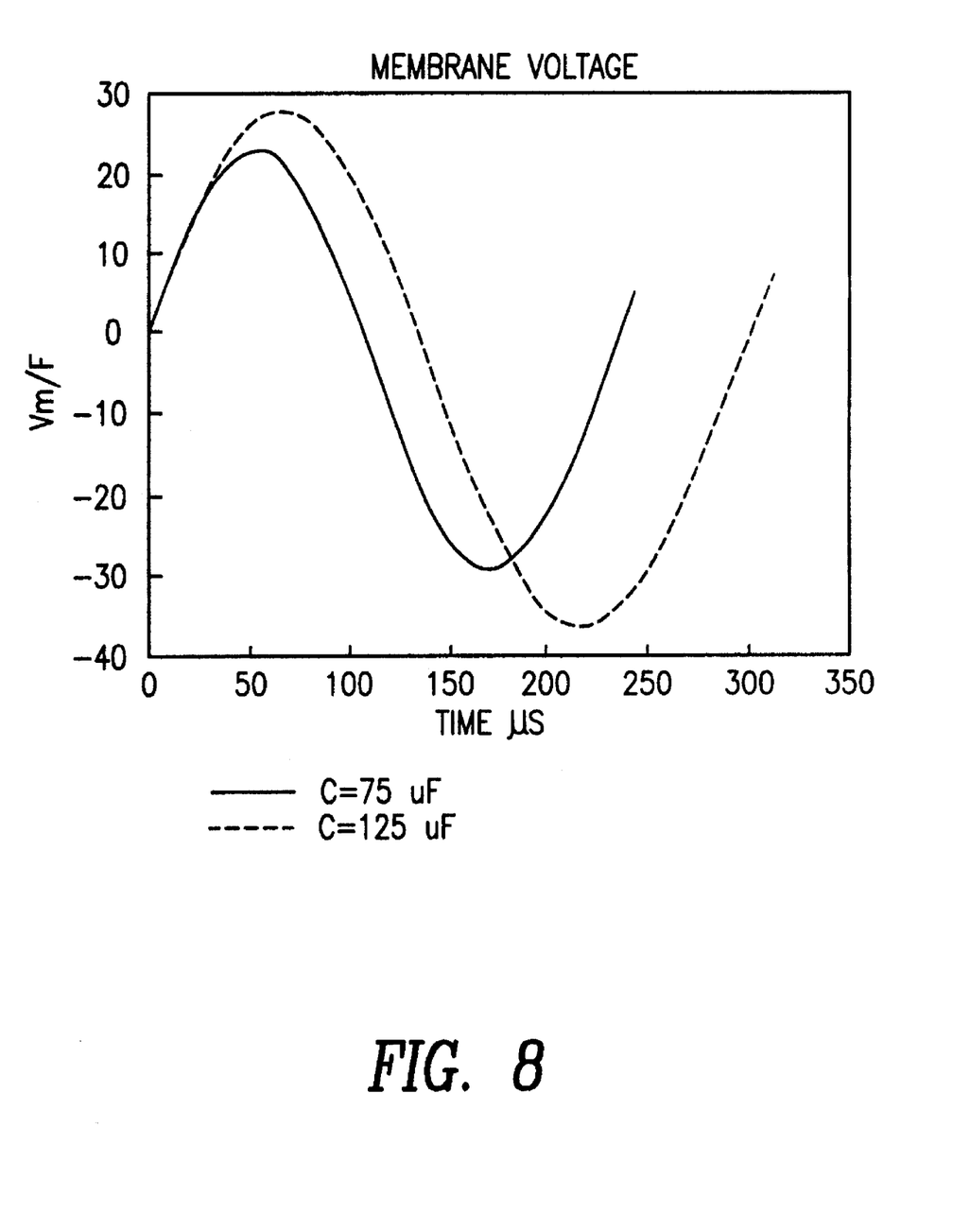
FIG. 8 is a graph representing how increasing the capacitance will deliver more effective stimulation essentially for all fibers.

Consider a 1200 V stimulator using a 20 μH inductor and a 12.6 mΩ resistor, operating on a nerve with a membrane time constant $\tau_m$=150 μs, with a magnetic circuit reluctance $\Re$=5.55*10⁶ H⁻¹. Allow the capacitance to vary from 75 μF to 125 μF. The membrane voltage as a function of time for these two cases is shown in FIG. 8. For a very large (and unrealistic) nerve fiber having a time constant $\tau_m$=10 μs, the two curves become identical. In fact, the only time the two cases become identical is when very large diameter fibers with very small time constants are involved. The key term determining this effect is the denominator in (17) or (18).

Figure 9:
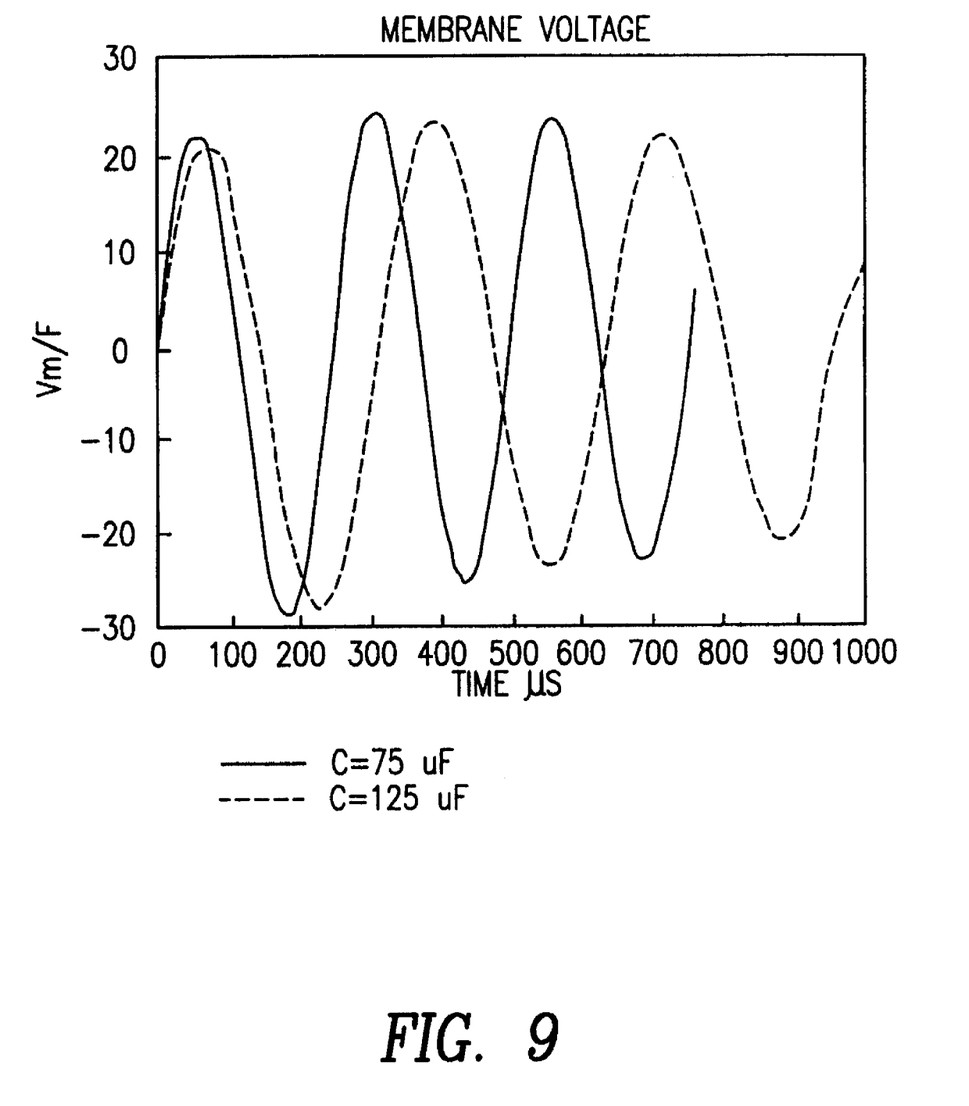
FIG. 9 is a graph showing an increase in capacitance while holding energy constant, the graph reveals that the lower capacitance is favored; the higher capacitive system has the lower stimulation because of lower resonant frequency.

Although FIG. 8 demonstrates the error of (28), the information can be misleading because it would suggest that an improved stimulator can be realized by increasing capacitance. A better comparison is performed by maintaining the same energy. The effect of changing capacitance while holding energy constant is shown in FIG. 9. This requires a downward adjustment in voltage when increasing the capacitance so that ½ C V² is constant. The second negative peak for the 75 μF system indicates its superiority, a result commensurate with its higher resonant frequency.

Additional peaks were drawn to illustrate generic principles about the circuit when it is allowed to fire repeatedly. Note that the second positive peak is higher than the first positive peak, but lower than the absolute value of the first negative peak. This is due to the negative decaying exponential caused by the membrane capacitance. The decay of the envelope of the sine wave is due to the resistive loss of the system.

Figure 10:
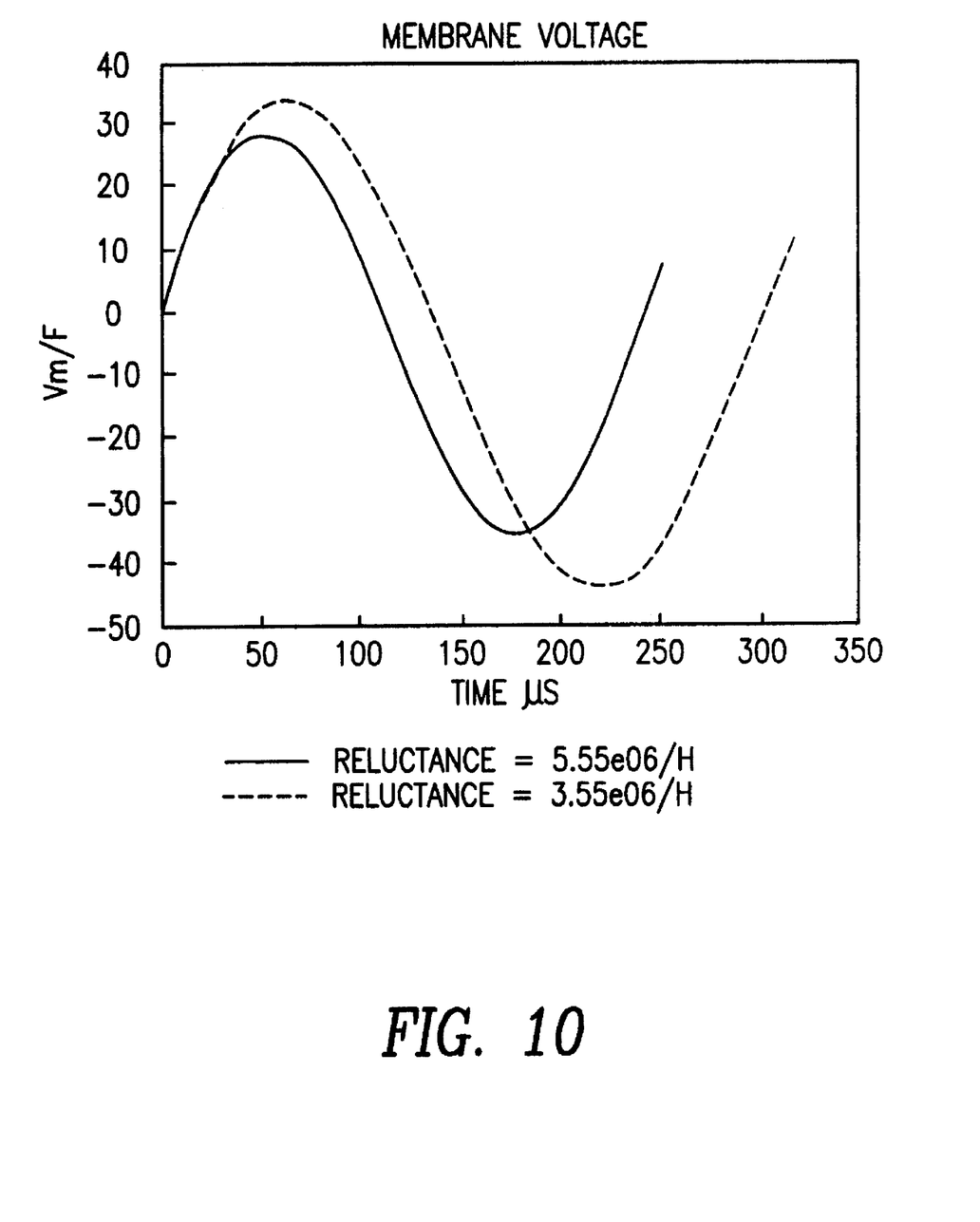
FIG. 10 is a graph showing that decreasing the reluctance $\mathfrak{R}$ decreases the resonant frequency, but increases the achievable membrane voltage.

A similar exercise can be conducted for reluctance; consider the same example, fixing the capacitance at 75 μF., the turns N at 11, and allowing the reluctance to vary from 3.55 to 5.55*10⁶ H⁻¹. Decreasing the reluctance will increase the inductance and decrease the resonant frequency. But the greater flux is a help as FIG. 10 clearly shows. This is a direct result of the multiplier in (17) and (18). Again when the membrane time constant reduces to 10 μs, the negative peaks become nearly synonymous. Like FIG. 9, this is a joule for joule comparison.

Figure 11:
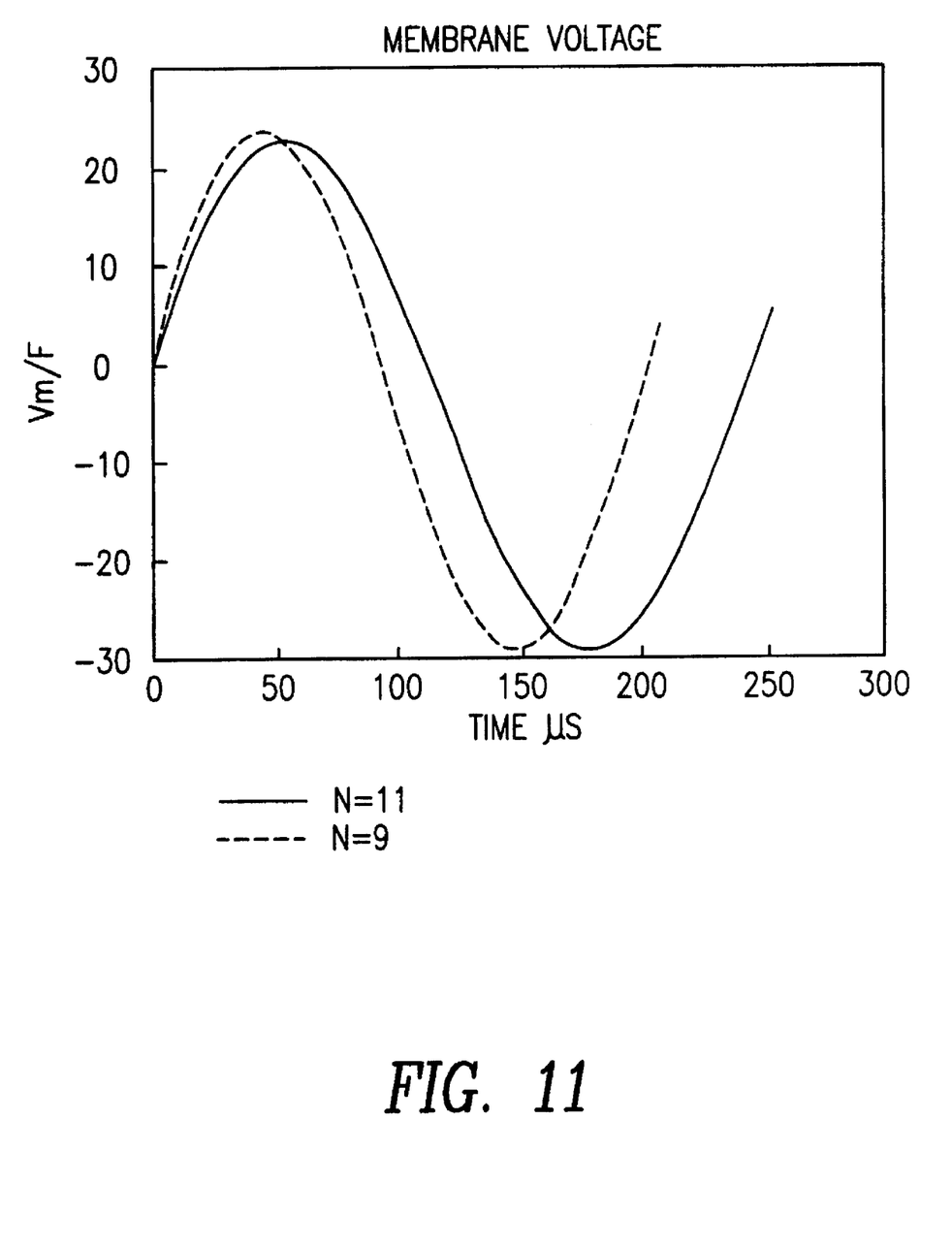
FIG. 11 is a graph showing that changing the number of turns does not affect the membrane voltage negative peak.

Consider next keeping the capacitor fixed at 75 μF., the reluctance at 5.55*10⁶ H⁻¹, and then allowing the turns to vary from N=9 to N=11. When the time constant of the fiber is 150 μs, changing the number of turns from 9 to 11 yields the two curves in FIG. 11. For normal nerve fibers with a time constant $\tau_m$=150 μs, this has no effect on the membrane voltage. Unrealistically fat fibers with a time constant of $\tau_m$10 μs would show that the lower number of turns would be preferred.

Figure 12:
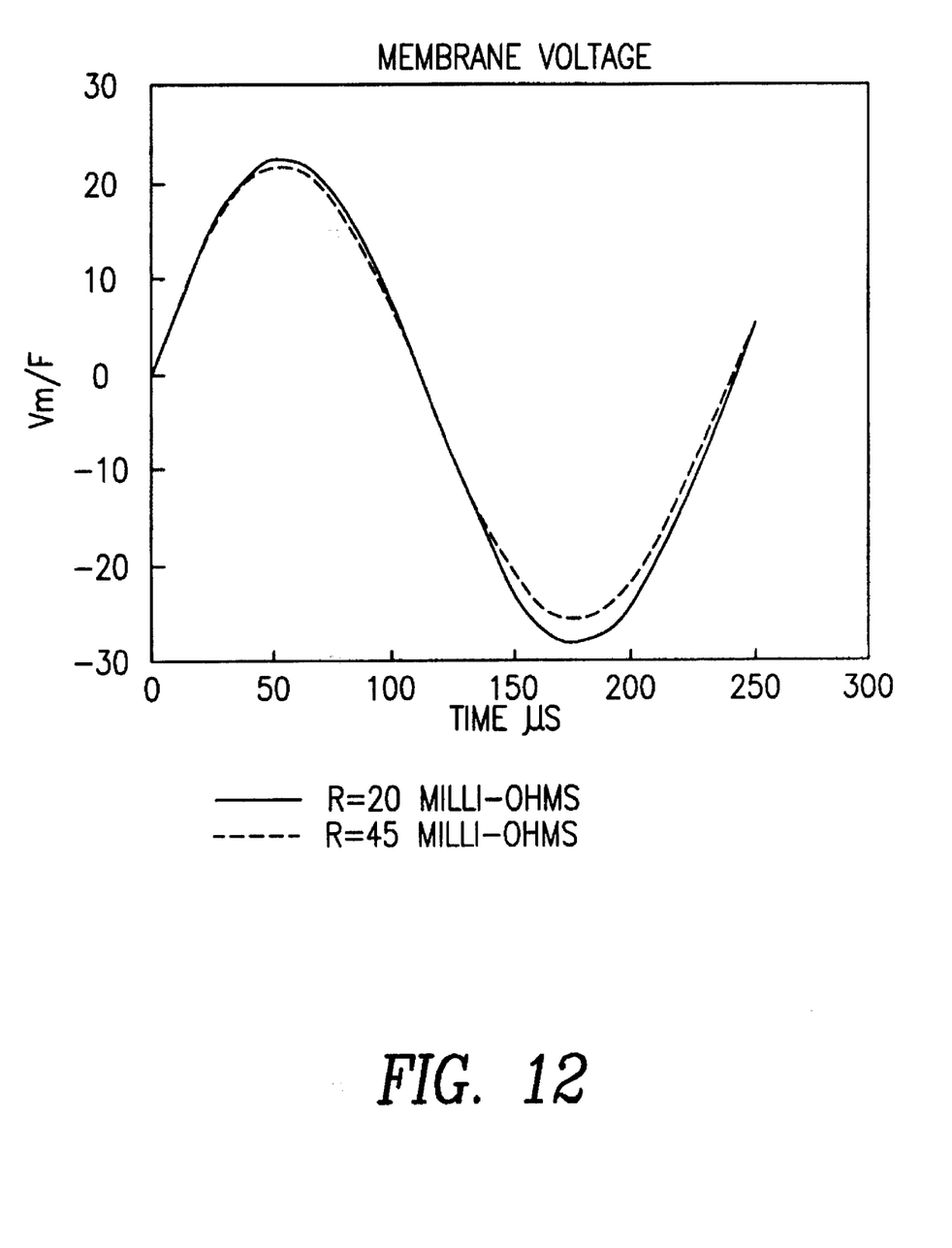
FIG. 12 is a graph showing that increasing resistance always lowers the stimulation capability.

As a final example consider fixing V=1200 V, N=11, $\Re$=5.55*10⁶ H⁻¹, C=75 μF., and allowing the resistance of the exciting circuit to range from 20 mΩ up to 45 mΩ, again keeping energy fixed. As expected FIG. 12 shows that the stimulation ability of the system will always drop as the exciting circuit resistance increases. The resistance of 20 mΩ approximates that of 6.09 m (20') of #10 gauge wire with no skin effect; the resistance 45 mΩ approximates the same wire treated as solid copper tube with skin effect near 8 kHz. The increase in resistance results in a 9.2% decrease in membrane stimulation voltage for the same energy.

In the preferred embodiment of the present invention, a coupled magnetic circuit—biological circuit—has been formulated in order to predict the conditions for optimizing nerve membrane stimulation. The circuit was formulated using Laplace transform theory. The results of the analysis yield the following four conclusions:
1. Maximize the energy
2. Minimize the reluctance
3. As budget and availability of devices develop, aspire towards a sufficiently high resonant frequency, near 10 kHz.
4. Use a biphasic excitation circuit, since the membrane capacitance will always insure a deeper membrane dip during the second portion of the wave.

Realistic components and regulations have voltage, current, and switching time limitations. Practical switching times for stud mounted SCR's are larger than those obtained from the theoretical suggestions of the model. The stimulation core must always be designed to deliver the minimum magnetic circuit reluctance under load. This implies a laminated high permeability, low saturation material having pole spans and head depths sufficient to avoid undue saturation. Once the maximum operating voltage, current, and minimum switching time are established, the capacitance, inductance, and number of turns for the stimulation core are fixed. Erroneous design considerations are avoided by considering the effect of the nerve membrane capacitance.

For a fixed energy, three changes that help increase membrane voltage are (1) keeping the reluctance low, (2) keeping the resonant frequency near 7.25–8.75 kHz, and (3)

keeping the exciting circuit resistance small. One method to achieve (2) is to lower the circuit capacitance C and increase the voltage V. Changing the number of turns for a constant energy system has no effect on membrane voltage by itself if the circuit resistance is kept the same; lowering the number of turns is only helpful in that it encourages a lower circuit resistance.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

REFERENCES

The disclosures of the following references are fully incorporated herein by reference.

1. Caldwell, John A., "Method and apparatus for magnetically stimulating neurons", U.S. Pat. No. 4,940,453, Jul. 10, 1990.
2. A. Barker, C. Graham, and I. Freeston, "Magnetic nerve stimulation: the effect of waveform on efficiency, determination of neural time constants, and the measurement of stimulator output", *Magnetic Motor Stimulation: Basic Principles and Clinical Experience*, EEG Supplemental 43, 1991, pp. 221–237.
3. R. Plonsey, Bioelectrical Phenomena, McGraw Hill, New York, 1969.
4. John Cadwell, "Optimizing Magnetic Stimulator Design", *Magnetic Motor Stimulation: Basic Principles and Clinical Experience*, EEG Supplement 43, 1991, pp. 238–248.
5. G. A. Mouchawar, J. A. Nyenhuis, J. D. Bourland, and L. A. Geddes, "Guidelines for energy efficient coils: coils designed for magnetic stimulation of the heart", *Magnetic Motor Stimulation Basic Principles and Clinical Experience*, EEG Supplement 43, 1991, pp. 255–267.
6. C. W. Hess, K. M. Rosler, R. O. Heckmann, H. P. Ludin, "Magnetic Stimulation of the Human Brain: Influence of size and shape of the stimulating coil", *Motor Disturbances II*, Academic Press Limited, London, U.K. 1990, pp. 31–42.
7. A. Cantano, P. Noel, "Transcranial Magnetic Stimulation: Interest in the excitation threshold", Acta Neurologica Belgica, vol. 97, 1997, p. 61.
8. G. Cerri, R. Deleo, F. Moglie, A. Schiavoni, "An accurate 3-D model for magnetic stimulation of the brain cortex", *Journal of Medical Engineering and Technology*, Vol. 1, 1995, pp. 7–16.
9. B. J. Roth and P. J. Basser, "A model of the stimulation of a nerve fiber by electromagnetic induction", *IEEE Transactions on Biomedical Engineering*, vol. 37, 1990, pp. 588–596.
10. P. J. Maccabee, S. S. Nagarajan, V. E. Amassian, D. M. Durand, R. Q. Cracco, A. Z. Szabo, A. Ahad, K. S. Lai and L. P Eberle. "Optimal polarity sequence for exciting human and porcine peripheral nerve with neuromagnetic stimuli: with computer simulation", *Journal of Physiology* (London), Vol. 513, No. 2, 1998, pp. 571–585.
11. M. S. George, "Re-animating the face: early writings by Duchenne and Darwin on the neurology of facial emotion expression", *J. Hist. Neurology*, vol.2, 1994, pp. 1–13.
12. G. A. Dudley, "Is electrical stimulation applicable to increase strength and power in normal humans?", in *Human Muscular Function During Dynamic Exercise*, ed. by P. Marconnet, B. Saltin, P. Komi, and J. Pootmans, Karger Book Series: Medicine and Sport Science, Karger Publications, Basel, 1996, pp. 71–81.
13. E. M. Wasserman, L. M. McShane, M. Hallett, and L. G. Cohen, "Noninvasive mapping of muscle representations in human cortex", *Electroencephalography and Clinical Neurophysiology*, vol. 85, 1992, pp. 1–8.
14. C. M. Epstein, J. K. Lah, K. Meador, J. D. Weissman, L. E. Gaitan, B. Dihenia, "Optimum stimulus parameters for lateralized suppression of speech with magnetic brain stimulation", *Neurology*, vol. 44, 1994, pp. 269–273.
15. A. Fleischman, K. Prolov, J. Abarbanel, R. H. Belmaker, "Effect of Transcranial magnetic stimulation on behavioral models of depression", *Brain Research*, vol. 699, 1995, pp. 130–132.
16. B. Greenberg, U. McCann, J. Benjamin, D. Murphy, "Repetitive TMS as a probe in Anxiety Disorders:. Theoretical Considerations and Case Reports", *CNS Spectrums*, vol.2, no. 1, 1997, pp. 47–52.

What is claimed is:

1. A method for nerve cell stimulation, comprising the steps of:

selecting an optimal frequency of a coupled magnetic circuit for construction of a magnetic nerve stimulator;

selecting an optimal reluctance of a coupled magnetic circuit for construction of a magnetic nerve stimulator;

selecting an optimal capacitance of a coupled magnetic circuit for construction of a magnetic nerve stimulator; and selecting an optimal winding resistance of a coupled magnetic circuit for construction of a magnetic nerve stimulator, wherein said optimal frequency, said optimal reluctance, said optimal capacitance, and said optimal winding resistance are selected to maximize stimulation of any type of nerve cell, and wherein said optimal frequency, said optimal reluctance, said optimal capacitance, and said optimal winding resistance are selected using a membrane voltage equation.

2. A method as claimed in claim 1 said membrane voltage equation being $$V_m(t) = f\sqrt{\frac{2W}{R}}\,\omega\tau_L \frac{(4\omega^2\tau_L^2 - 1)\left(e^{-\frac{t}{2\tau_L}}\cos(\beta) + \frac{e^{-\frac{t}{2\tau_L}}(2\tau_L\tau_m\omega^2 - 1)\sin(\beta)}{\sqrt{4\omega^2\tau_L^2 - 1}} - e^{-\frac{t}{\tau_m}}\right)}{4\omega^4\tau_m^2\tau_L^3 + \omega^2(4\tau_L^3 - \tau_m^2\tau_L) + (\tau_m - \tau_L)},$$

where $\beta \equiv \frac{1}{2}\sqrt{\frac{4\omega^2\tau_L^2 - 1}{\tau_L^2}}\,t$.

3. A method as claimed in claim 1 said membrane voltage equation being $$V_m = f\omega \sqrt{\frac{2W}{R}} \frac{\left(\cos(\omega t) + \omega \tau_m \sin(\omega t) - e^{-\frac{t}{\tau_m}}\right)}{1 + \omega^2 \tau_m^2}.$$

4. A method as claimed in claim 1, further comprising the step of constructing said magnetic nerve stimulator.

5. A method for optimizing nerve membrane stimulation, comprising the steps of:
   maximizing the energy of a coupled magnetic circuit;
   minimizing the reluctance of a coupled magnetic circuit;
   selecting a high resonant frequency of a coupled magnetic circuit; and
   using a biphasic excitation circuit,
   wherein said resonant frequency is within the range of 7.25–8.75 kHz.

6. A method according to claim 5, further comprising the step of keeping the resistance of a coupled magnetic circuit small.

7. A method for optimizing nerve membrane stimulation, comprising the steps of:
   maximizing the energy of a coupled magnetic circuit;
   minimizing the reluctance of a coupled magnetic circuit;
   selecting a high resonant frequency of a coupled magnetic circuit; and
   using a biphasic excitation circuit,
   wherein said high resonant frequency is 10 kHz.

8. A method according to claim 7, further comprising the step of keeping the resistance of a coupled magnetic circuit small.

9. A method for optimizing nerve membrane stimulation, comprising the steps of:
   maximizing the energy of a coupled magnetic circuit;
   minimizing the reluctance of a coupled magnetic circuit;
   selecting a high resonant frequency of a coupled magnetic circuit; and
   using a biphasic excitation circuit,
   wherein said step of minimizing reluctance further comprises using a laminated high permeability/low saturation material.

10. A method according to claim 9, further comprising the step of keeping the resistance of a coupled magnetic circuit small.

* * * * *